United States Patent [19]

Iio

[11] Patent Number: 5,665,843
[45] Date of Patent: Sep. 9, 1997

[54] ALLYLBIGUANIDE POLYMER AND METHOD OF PRODUCING SAME

[75] Inventor: Kokoro Iio, Ushiku, Japan

[73] Assignee: Director-General of Agency of Industrial Science and Technology, Japan

[21] Appl. No.: 595,578

[22] Filed: Feb. 1, 1996

[30] Foreign Application Priority Data

Feb. 13, 1995 [JP] Japan ................................. 7-024036

[51] Int. Cl.$^6$ ......................................... C08F 20/52
[52] U.S. Cl. ..................... 526/310; 525/328.2; 525/374; 525/381; 525/382
[58] Field of Search .............. 526/310; 525/374, 525/381, 382, 328.2

[56] References Cited

U.S. PATENT DOCUMENTS 5,260,385  11/1993  Iio ..................................... 525/328.2

*Primary Examiner*—Fred Zitomer
*Attorney, Agent, or Firm*—Lorusso & Loud

[57] ABSTRACT

An allylbiguanide polymer having the following formula:

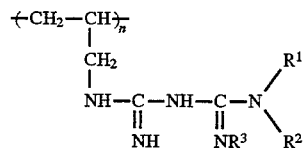

wherein $R^1$, $R^2$ and $R^3$ stand, independently of each other, for a hydrogen atom, a substituted or non-substituted aliphatic hydrocarbon group, a substituted or non-substituted alicyclic hydrocarbon group or a substituted or non-substituted aromatic group and n represents an average degree of polymerization of at least 2, or an acid addition salt thereof. The polymer may be obtained by polymerizing an allylbiguanide compound of the formula shown below or an acid addition salt thereof at a pH of 5 or less,

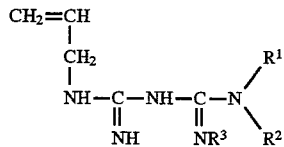

wherein $R^1$, $R^2$ and $R^3$ have the same meaning as above.

8 Claims, 1 Drawing Sheet

ALLYLBIGUANIDE POLYMER AND METHOD OF PRODUCING SAME

BACKGROUND OF THE INVENTION

This invention relates to an allylbiguanide polymer and to a process for the preparation thereof.

One known process for the preparation of an allylbiguanide polymer includes reacting a polyallylamine with guanyl-O-alkylisourea or a salt thereof (U.S. Pat. No. 5,260,385). With this method, however, the amino groups of the polyallylamine are not easily substituted by biguanide groups so that the allylbiguanide polymer obtained contains a significant amount of unsubstituted amine groups.

SUMMARY OF THE INVENTION

It is, therefore, an object of the present invention to provide a novel allylbiguanide polymer which is substantially free of aminomethyl ($-CH_2-NH_2$) groups branched directly from the polymer skeleton.

Another object of the present invention is to provide a simple process which can produce the above allylbiguanide polymer.

In accordance with the present invention there is provided an allylbiguanide polymer having the following formula (I):

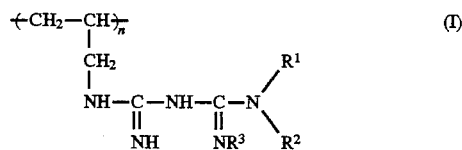

wherein $R^1$, $R^2$ and $R^3$ stand, independently of each other, for a hydrogen atom, a substituted or non-substituted aliphatic hydrocarbon group, a substituted or non-substituted alicyclic hydrocarbon group or a substituted or non-substituted aromatic group and n represents an average degree of polymerization of at least 2, or an acid addition salt thereof.

The present invention also provides a process for the preparation of an allylbiguanide polymer having the above formula (I), which includes polymerizing an allylbiguanide compound at a pH of 5 or less, the allylbiguanide compound being a compound having the following formula (II):

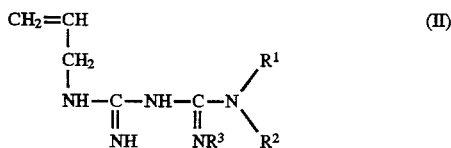

wherein $R^1$, $R^2$ and $R^3$ have the same meaning as above, or an acid addition salt thereof.

BRIEF DESCRIPTION OF THE DRAWINGS

Other objects, features and advantages of the present invention will become apparent from the detailed description of the preferred embodiments of the invention which follows, when considered in the light of the accompanying drawing, in which.

DETAILED DESCRIPTION OF THE EMBODIMENTS OF THE INVENTION

Figure 1:
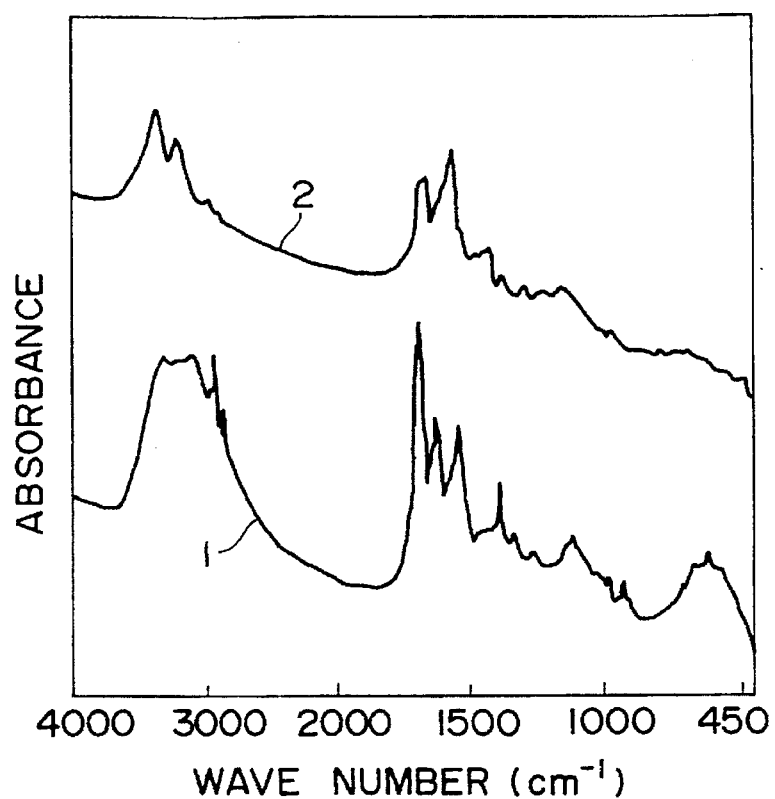
FIG. 1 shows IR spectra of the raw material monomer and polybiguanide obtained therefrom in Example 1.

In the process of the present invention, the allylbiguanide compound of the formula (II) is polymerized preferably in the presence of an azo compound as a polymerization initiator. In the formula (II), $R^1$, $R^2$ and $R^3$ are each preferably a hydrogen atom, a substituted or non-substituted alkyl group, a substituted or non-substituted cycloalkyl group, a substituted or non-substituted aryl group or a substituted or non-substituted aralkyl group. The alkyl group may be $C_1-C_{18}$ alkyl such as a methyl group, an ethyl group, a propyl group, a hexyl group, a dodecyl group, a stearyl group or an oleyl group. The cycloalkyl group may be, for example, a cyclobutyl group, a cyclopentyl group, a cyclohexyl group, a cyclooctyl group, a cyclohexylmethyl group, a cyclohexylethyl group or a methylcyclohexyl group. The aryl group may be, for example, a phenyl group, a tolyl group, a xylyl group of a naphthyl group. The aralkyl group may be, for example, a benzyl group or a phenethyl group. The alkyl, cycloalkyl, aryl and aralkyl group may possess one or more inert substituents such as an alkoxy group, e.g. a methoxy group, an ethoxy group or a butoxy group; an aryloxy group, e.g. a phenoxy group, a tolyloxy group or a naphthyloxy group; a hydroxyl group or a carboxyl group.

The allylbiguanide compound may be a salt of the compound of the formula (II) with an acid. The acid salt may be an inorganic acid salt such as a hydrochloride, hydrobromide, a hydroiodide, a sulfate, a methylbisulfate or a phosphate; or an organic acid salt such as a p-toluenesulfonate, an acetate, an oxalate or a citrate.

The allylbiguanide compound used as a raw material monomer in the process if the present invention may be obtained by reacting a guanyl-O-methyiisourea or an addition salt thereof with allylamine at a temperature of 0°–100° C., preferably 20°–40° C. in an inert gas atmosphere:

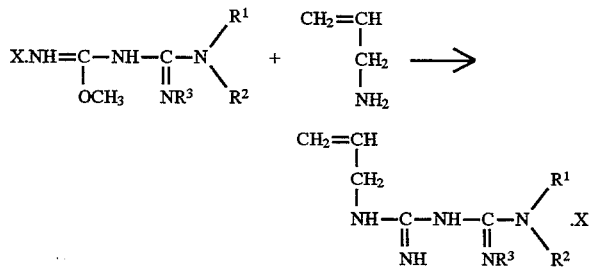

wherein $R^1$, $R^2$ and $R^3$ are as defined above and X is an acid or may be absent.

The azo compound is preferably used in the present invention as a polymerization initiator. Illustrative of suitable azo compounds are 2,2'-azobis(2-amidinopropane) dihydrochloride, dimethyl 2,2'-azobisisobutyrate, 2-cyano-2-propylazoformamide, 2,2'-azobis[2-(5-methyl-2-imidazoline-2-yl)propane]dihydrochloride, 2,2'-azobis(2-methylbutyronitrile), 2,2'-azobisisobutyronitrile, 4,4'-azobis( 4-cyanovaleric acid), 2,2'-azobis[2-(2-imidazoline-2-yl)propane]dihydrochloride, 2,2'-azobis[2-(2-imidazoline-2-yl)propane], 2,2'-azobis{2-methyl-N-[1,1'-bis(hydroxymethyl)-2-hydroxyethyl]propionamide}, 2,2'-azobis[2-methyl-N-(2-hydroxymethyl)propionamide, 2,2'-azobisisobutyramide dihydrate and 2,2'-azobis[2-(hydroxymethyl)propionitrile]. The azo compound is generally used in an amount of 0.1–10% by weight, preferably 1–6% by weight, based on the weight of the allylbiguanide compound.

The allylbiguanide compound and the azo compound are preferably dissolved in a polar solvent, preferably an aqueous solvent. Illustrative of suitable polar solvents are water, alcohols, dimethylsulfoxide, dimethylforamide, organic acids and mixtures thereof. The alcohol may be, for example, methanol, ethanol, propanol or ethylene glycol, while the organic acid may be, for example, acetic acid, propionic acid or lactic acid. The polar solvent is generally used in an amount of 1–100 parts by weight, preferably 2–10 parts by weight, per part by weight of the allylbiguanide compound.

The polymerization of the allylbiguanide compound is carried out in an acidic condition. Thus, it is important that the allylbiguanide compound should be reacted at a pH of 5 or less, preferably at a pH of 2.4 or less. The acid used for establishing such an acidic condition is preferably an inorganic acid such as hydrochloric acid, sulfuric acid or phosphoric acid. The concentration of the acid in the polar solvent solution is preferably at least 0.01 mole/liter, preferably 0.1 mole/liter. The polymerization may be carried out in an unhydrous condition or without a polar solvent, however.

The allylbiguanide compound (raw material monomer) is reacted, optionally in the presence of the azo compound (initiator), at a temperature of generally 30°–100° C., preferably 40°–70° C., to yield an allylbiguanide polymer of the formula (I). Depending upon the reaction time and pH, the average polymerization degree (n in the formula (I)) may vary as desired. Not only an oligomer having an average polymerization degree (n) of 2–10 but also a higher molecular weight polymer having a number average molecular weight of about 2,000 to about 1,000,000 may be obtained.

The allylbiguanide polymer may be utilized for various applications, for example, as a germicide, an algaecide, an antibacterial agent, an agglomerating agent and an antistatic agent.

The following examples will further illustrate the present invention.

REFERENCE EXAMPLE 1

Preparation of Allylbiguanide Hydrochloride:

Into 3 ml of ethanol were dissolved 5 g of guanyl-O-methylisourea hydrochloride and 3 ml of allylamine. The resulting solution was reacted at room temperature for 24 hours in a nitrogen stream. The reaction mixture was then filtered and the precipitates were washed with ethanol to give 3.14 g of allylbiguanide hydrochloride as needle like crystals (m.p.: 178°–179° C.).

EXAMPLE 1

Allylbiguanide hydrochloride (1.5 g) obtained in Reference Example 1 and 0.03 g of 2,2'-azobis(2-amidinopropane) dihydrochloride were charged in a glass tube and dissolved in 2.2 ml of 6N hydrochloric acid. The tube was sealed under vacuum and then heated at a temperature of 50°±3° C. for 42 hours for the polymerization of allylbiguanide. Thereafter, the reaction mixture was poured into acetone to precipitate the polymer product. The polymer product (1.5 g) was purified by a method including dissolving the polymer in a minimum quantity of water and precipitating the polymer with acetone. The purified polymer was analyzed to reveal that the polymer was polyallylbiguanide hydrochloride. The elementary analysis of the polymer gave: C: 29.68%, H: 6.26%, N: 28.78%, Cl: 28.62%. The gel permeation chromatography revealed that the polymer had a number average molecular weight of 9,600, a weight average molecular weight of 9,900 and a Z-average molecular weight of 10,200. The infrared absorption spectrum of the polymer is shown in FIG. 1 (designated as 1) together with that of the allylbiguanide monomer. (designated as 2).

EXAMPLE 2

Allylbiguanide hydrochloride (1.5 g) obtained in Reference Example 1 and 0.03 g of 2,2'-azobis(2-amidinopropane) dihydrochloride were charged in a glass tube and dissolved in 4.4 ml of 85 wt % phosphoric acid. The tube was sealed under vacuum and then heated at a temperature of 50°±3° C. for 42 hours for the polymerization of allylbiguanide. Thereafter, the reaction mixture was poured into acetone to precipitate the polymer product. The polymer product was purified by a method including dissolving the polymer in a minimum quantity of water and precipitating the polymer with acetone. The purified polymer was analyzed to reveal that the polymer was polyallylbiguanide hydrochloride. The gel permeation chromatography revealed that the polymer had a number average molecular weight of 6,100, a weight average molecular weight of 7,100 and a Z-average molecular weight of 8,700.

EXAMPLE 3

Allylbiguanide hydrochloride (1.8 g) obtained in Reference Example 1 and 0.03 g of 2,2'-azobis(2-amidinopropane) dihydrochloride were charged in a glass tube and dissolved in 2.2 ml of 6N hydrochloric acid. After replacing the atmosphere within the tube with nitrogen gas, the tube was sealed under vacuum and then heated at a temperature of 50°–55° C. for 3 hours for the polymerization of allylbiguanide. Thereafter, the reaction mixture was poured into acetone to precipitate the product. The product was purified by a method including dissolving the polymer in a minimum quantity of water and precipitating the polymer with acetone. The purified polymer was analyzed by the gel permeation chromatography to reveal that the product was a mixture of a dimer and a trimer of allylbiguanide.

EXAMPLE 4

Figure 2:
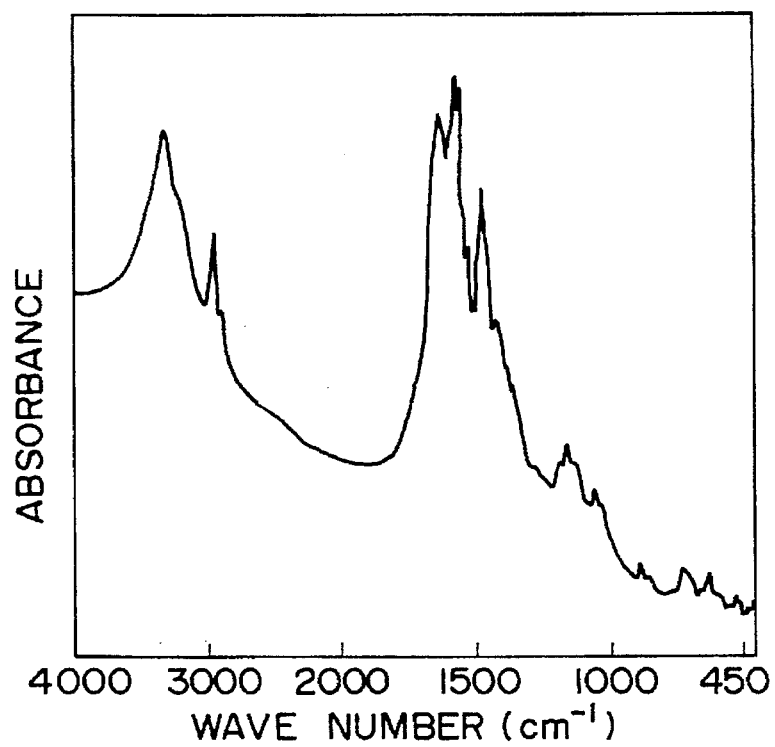
FIG. 2 shows an IR spectra of the raw material monomer and polybiguanide obtained in Example 4.

$N^1,N^2$-Dimethylallylbiguanide hydrochloride (1.95 g, the compound of the above formula (II) in which $R^1$ and $R^2$ each represent a methyl group and $R^3$ represents a hydrogen atom) and 0.037 g of 2,2'-azobis(2-amidinopropane) dihydrochloride were charged in a glass tube and dissolved in 2 mi of 12N hydrochloric acid. The tube was sealed under vacuum and then heated at a temperature of 50°–55° C. for 50 hours for the polymerization of the biguanide. Thereafter, the reaction mixture was poured into acetone to precipitate 2.34 g of a polymer product. The polymer product was purified in the same manner as that in Example 1. The purified polymer was analyzed to reveal that the polymer was poly($N^1,N^2$-dimethylallylbiguanide)hydrochloride. The infrared spectrum of the polymer is shown in FIG. 2. The gel permeation chromatography revealed that the polymer had a number average molecular weight of 10,800, a weight average molecular weight of 11,100 and a Z-average molecular weight of 11,300.

EXAMPLE 5

Allylbiguanide hydrochloride (0.5 g) obtained in Reference Example 1 and 0.0047 g of 2,2'-azobis(2-amidinopropane)dihydrochloride were charged in a glass tube and dissolved in 2 ml of 6N hydrochloric acid. The tube was then heated in air (while maintaining the tube in an open state) at a temperature of 50°–55° C. for 50 hours for the polymerization of allylbiguanide. Thereafter, the reaction mixture was poured into acetone to precipitate the polymer product. The polymer product (0.5 g) was purified in the same manner as that in Example 1. The purified polymer was analyzed to reveal that the polymer was polyallylbiguanide hydrochloride. The gel permeation chromatography revealed that the polymer had a number average molecular weight of 10,500, a weight average molecular weight of 11,800 and a Z-average molecular weight of 11,600.

EXAMPLE 6

Allylbiguanide hydrochloride (0.5 g) obtained in Reference Example 1 was charged in a glass tube and dissolved in 2 ml of 12N hydrochloric acid. The tube was sealed under vacuum and then heated at a temperature of 50°-55° C. for 50 hours for the polymerization of allylbiguanide. Thereafter, the reaction mixture was poured into acetone to precipitate the polymer product. The polymer product (0.54 g) was purified in the same manner as that in Example 1. The purified polymer was analyzed to reveal that the polymer was polyallylbiguanide hydrochloride. The gel permeation chromatography revealed that the polymer had a number average molecular weight of 9,900, a weight average molecular weight of 10,100 and a Z-average molecular weight of 10,400.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. An allylbiguanide polymer consisting essentially of recurring units having the following formula:

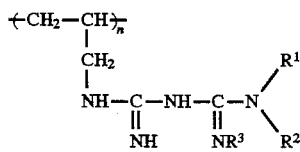

wherein $R^1$, $R^2$ and $R^3$ stand, independently of each other, for a hydrogen atom, a substituted or non-substituted aliphatic hydrocarbon group, a substituted or non-substituted alicyclic hydrocarbon group or a substituted or non-substituted aromatic group and n represents an average degree of polymerization of at least 2, or an acid addition salt thereof.

2. An allylbiguanide polymer as claimed in claim 1, wherein $R^1$, $R^2$ and $R^3$ stand, independently of each other, for a hydrogen atom, a substituted or non-substituted alkyl group, a substituted or non-substituted cycloalkyl group, a substituted or non-substituted aryl group or a substituted or non-substituted aralkyl group.

3. A process for the preparation of an allylbiguanide polymer consisting essentially of recurring units having the following formula:

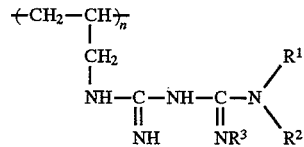

said process comprising polymerizing an allylbiguanide compound or an acid addition salt thereof at a pH of 5 or less, said allylbiguanide compound having the following formula:

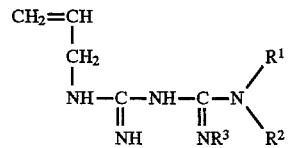

wherein $R^1$, $R^2$ and $R^3$ have the same meaning as above.

4. A process as claimed in claim 3, wherein said polymerizing is performed in the presence of an azo compound.

5. A process as claimed in claim 4, wherein said azo compound is selected from the group consisting of 2,2'-azobis(2-amidinopropane)dihydrochloride, dimethyl 2,2'-azobisisobutyrate, 2-cyano-2-propylazoformamide, 2,2'-azobis[2-(5-methyl-2-imidazoline-2-yl)propane] dihydrochloride, 2,2'-azobis(2-methylbutyronitrile), 2,2'-azobisisobutyronitrile, 4,4'-azobis(4-cyanovaleric acid), 2,2'-azobis[2-(2-imidazoline-2-yl)propane]dihydrochloride, 2,2'-azobis[2-(2-imidazoline-2-yl)propane], 2,2'-azobis{2-methyl-N-[1,1'-bis(hydroxymethyl)-2-hydroxyethyl] propionamide}, 2,2'-azobis[2-methyl-N-(2-hydroxymethyl) propionamide, 2,2'-azobisisobutyramide dihydrate and 2,2'-azobis[2-(hydroxymethyl)propionitrile].

6. A process as claimed in claim 3, wherein said polymerizing is performed in a polar solvent.

7. A process as claimed in claim 5, wherein said polar solvent is an aqueous hydrochloric acid, an aqueous phosphric acid or an aqueous sulfuric acid.

8. A process as claimed in claim 3, wherein said polymerizing is performed at a pH of 2.4 or less.

* * * * *

UNITED STATES PATENT AND TRADEMARK OFFICE
CERTIFICATE OF CORRECTION

PATENT NO. : 5,665,843
DATED : September 9, 1997
INVENTOR(S) : Kokoro IIO

It is certified that error appears in the above-indentified patent and that said Letters Patent is hereby corrected as shown below:

Col. 6, line 45, "5" should read --6--.

Signed and Sealed this

Third Day of November, 1998

*Attest:*

BRUCE LEHMAN

*Attesting Officer*  Commissioner of Patents and Trademarks